(12) United States Patent
Liu

(10) Patent No.: US 9,596,886 B2
(45) Date of Patent: Mar. 21, 2017

(54) ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 630 days.

(21) Appl. No.: 14/057,072

(22) Filed: Oct. 18, 2013

(65) Prior Publication Data

US 2015/0027465 A1 Jan. 29, 2015

(30) Foreign Application Priority Data

Jul. 26, 2013 (CN) .................... 2013 2 0465635 U

(51) Int. Cl.
*A24F 47/00* (2006.01)
*A61M 15/06* (2006.01)

(52) U.S. Cl.
CPC ............ *A24F 47/008* (2013.01); *A61M 15/06* (2013.01)

(58) Field of Classification Search
CPC ....................................................... A24F 47/00
See application file for complete search history.

(56) References Cited

U.S. PATENT DOCUMENTS

| | | | | |
|---|---|---|---|---|
| 4,942,888 A | * | 7/1990 | Montoya ................. | A24B 15/14 131/352 |
| 5,129,408 A | * | 7/1992 | Jakob ..................... | A24B 15/14 131/352 |
| 2005/0172976 A1 | * | 8/2005 | Newman ................ | A24F 47/008 131/194 |
| 2008/0017206 A1 | * | 1/2008 | Becker .................. | A23L 1/22025 131/276 |
| 2013/0192613 A1 | * | 8/2013 | Combs .................. | D04H 1/4258 131/202 |
| 2013/0298905 A1 | * | 11/2013 | Levin .................... | A24F 47/008 128/202.21 |
| 2014/0041655 A1 | * | 2/2014 | Barron .................. | A61M 11/042 128/202.21 |

FOREIGN PATENT DOCUMENTS

| | | | | |
|---|---|---|---|---|
| CN | 203058273 U | * | 7/2013 | |
| GB | 2497536 A | * | 6/2013 | ........... A24F 47/002 |

OTHER PUBLICATIONS

Machine translation of CN203058273U. Original publication Jul. 17, 2013. Filed Dec. 12, 2012.*

* cited by examiner

*Primary Examiner* — Jason L Lazorcik
*Assistant Examiner* — Cynthia Szewczyk
(74) *Attorney, Agent, or Firm* — Tim Tingkang Xia, Esq.; Locke Lord LLP

(57) ABSTRACT

An electronic cigarette is provided, comprising a non-metal outer sleeve, a first paint layer is configured along outer wall of the outer sleeve. The electronic cigarette of the application provides a first paint layer arranged on the outer sleeve to replace the stickers to make function of heat insulation, protection and aesthetic function, has the advantages of simple procedure, high production efficiency and has the beneficial effect of meeting the personalized needs of users.

1 Claim, 4 Drawing Sheets

ELECTRONIC CIGARETTE

CROSS-REFERENCE TO RELATED APPLICATION

This application claims priority of application No. 201320465635.X, filed on Jul. 26, 2013 in the Intellectual Property Office of The Republic of China, which is incorporated by reference herein in its entirety.

FIELD OF THE INVENTION

The present application relates to the field of electrical products, and more particularly relates to an electronic cigarette.

BACKGROUND OF THE INVENTION

Electronic cigarettes are mainly used for quitting smoking and substituting cigarettes. At present, a structure of an electronic cigarette on the market generally comprises an outer sleeve, a battery assembly and an atomizer assembly. The battery assembly supplies power to the atomizer assembly to generate smoke for a user to smoke, and to simulate smoking.

In the prior art, appearance of the outer sleeve of the electronic cigarette is stuck on one kind of stickers to make function of heat insulation and anti-slipping. The sticking process of production is complicated and inefficient, and is difficult to meet the personalized needs of different users.

SUMMARY OF THE INVENTION

The objective of the present application is to provide an electronic cigarette with a high-efficient and simple production process and can meet the personalized needs of different users, aiming at the above-mentioned drawbacks that the process of production of the electronic cigarette in the prior art has complicated procedure and low production efficiency, when using the sticker on the outer sleeve of the electronic cigarette to make the function of heat insulation and anti-slipping.

The technical solutions of the present application for solving the technical problems are as follows:

In one aspect, an electronic cigarette comprises a non-metal outer sleeve and a first paint layer configured along outer wall of the outer sleeve.

In one embodiment, at least one containing groove containing the first paint layer forms on the outer wall of the outer sleeve. The containing grooves are arranged axially along the outer wall of the outer sleeve and are circumferential grooves, the grooves extend to the outer sleeve at both two ends, the first paint layer is arranged in the grooves.

In another embodiment, the containing grooves are multiple grooves arranged axially along the outer wall of the outer sleeve separately and throughout two ends of the outer sleeve, and the first paint layer is contained at each groove.

In a further embodiment, the containing grooves are multiple grooves arranged along the outer wall of the outer sleeve radially separately and surround the outer sleeve, and the first paint layer is contained at each groove.

In the above embodiments, paint of the first paint layer is UV consolidation paint or rubber paint. A thickness of the first paint layer is the same as a depth of the containing grooves. The thickness of the first paint layer ranges from 0.08 mm to 0.15 mm.

In additional embodiment, the outer sleeve comprises an atomizer sleeve and a battery sleeve detachably connected to the atomizer sleeve, an atomizer assembly is configured in the atomizer sleeve, a battery assembly is configured in the battery sleeve, the first paint layer is arranged on the area, corresponding to the atomizer assembly, of outer wall of the atomizer sleeve.

The outer sleeve further comprises a cigarette end part at one end of the battery sleeve, the end is far away from the atomizer sleeve, the cigarette end part is provided with a third paint layer, paint of the third paint layer is luminous paint.

In a possible embodiment, the electronic cigarette also comprises a second paint layer for setting images and/or logos on the first paint layer. In another example of this embodiment, the electronic cigarette also comprises a second paint layer for setting images and/or logos, the first paint layer and the second paint layer are arranged in parallel on the outer wall of the outer sleeve.

In another possible embodiment, the outer sleeve is provided with a suction nozzle part, the suction nozzle part is covered with stickers, and the stickers and the first paint layer are coaxially juxtaposed.

When implementing the electronic cigarette of the present application, the following advantageous effects can be achieved: the electronic cigarette of the application provides a first paint layer arranged on the outer sleeve to replace the stickers to make function of heat insulation, protection and aesthetic function, has the advantages of simple procedure, high production efficiency and has the beneficial effect of meeting the personalized needs of users.

BRIEF DESCRIPTION OF THE DRAWINGS

The present application will be further described with reference to the accompanying drawings and embodiments in the following, in the accompanying drawings.

DETAILED DESCRIPTION OF THE PREFERRED EMBODIMENT

To make the technical feature, objective and effect of the present application be understood more clearly, now the specific implementation of the present application is described in detail with reference to the accompanying drawings and embodiments.

Figure 1:
FIG. 1 is a structural schematic view of an electronic cigarette of a first embodiment of the present application.

As shown in FIG. 1, one of the preferred embodiments of the present application to provide an electronic cigarette, which comprises a non-metal outer sleeve 1 and a first paint layer 2. The non-metal outer sleeve 1 makes the electronic cigarette lighter, feel better, and the cost can be saved. An atomizer assembly (not shown) and a battery assembly (not shown) are arranged inside the outer sleeve 1. All external wall of outer sleeve 1 is covered with the first paint layer 2. Paint is sprayed or printed on the outer wall of the outer sleeve 1 to form the first paint layer 2. The first paint layer 2 can make the outer sleeve 1 have the function of heat insulation, non-slipping, makes the outer sleeve 1 more beautiful and feel better. And spraying or printing paint compared to sticking stickers has simpler procedure and higher production efficiency.

Understandably, paint of the first paint layer 2 is UV consolidation paint or rubber paint and so on. The UV consolidation paint is a kind of paint conforming to current environmental protection, does not contain any volatile substances. Using of the UV consolidation paint makes the electronic cigarette more green, healthy, and environmental. The rubber paint is printed on surface of the outer sleeve 1, feel of the rubber paint is exquisite, and smooth, appearance of the rubber paint is elegant and solemn. The rubber paint has scratch resistance and weather resistance, excellent wear resistance. The rubber paint conforms to green environmental protection printing, has no damage to human body.

Figure 2:
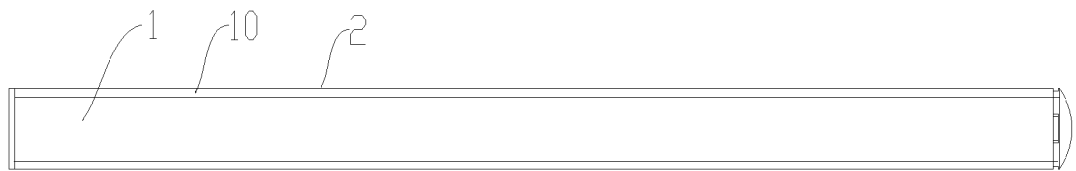
FIG. 2 is a structural schematic view of an electronic cigarette of a second embodiment of the present application.

FIG. 2 is a structural schematic view of an electronic cigarette of a second embodiment of the present application. In FIG. 2, there is at least one containing grooves 10, used for containing the first paint layer 2, forming on the outer wall of the outer sleeve 1. The containing grooves 10 extend axially along the outer wall of the outer sleeve 1 and are circumferential grooves (unlabeled), the grooves extend to two ends of the outer sleeve 1, namely, the outer wall of the outer sleeve 1 is completely covered with the grooves, the first paint layer 2 is arranged in the grooves.

Figure 3:
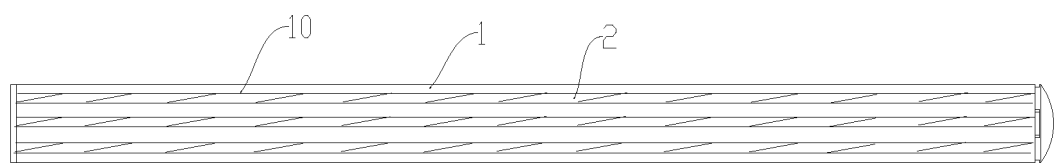
FIG. 3 is a structural schematic view of an electronic cigarette of a third embodiment of the present application.

FIG. 3 is a structural schematic view of an electronic cigarette of a third embodiment of the present application. In FIG. 3, the first paint layer 2 can only covers part of the outer wall of the outer sleeve 1, in this embodiment, the containing grooves 10 can be multiple grooves configured separately axially along the outer wall of the outer sleeve 1, the first paint layer 2 are respectively contained in each groove.

Figure 4:
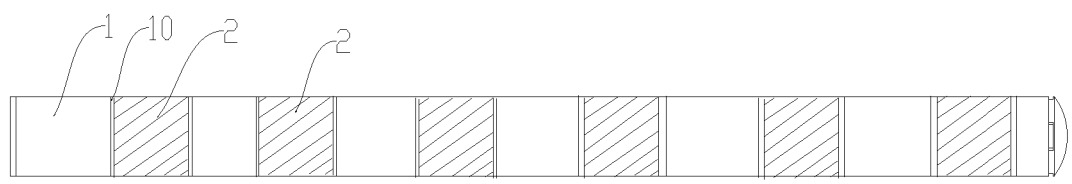
FIG. 4 is a structural schematic view of an electronic cigarette of a fourth embodiment of the present application.

FIG. 4 is a structural schematic view of an electronic cigarette of a fourth embodiment of the present application. In FIG. 4, the containing grooves 10 can be multiple grooves configured separately radially along the outer wall of the outer sleeve 1, the first paint layer 2 is respectively contained in each groove.

Advantageously, in the above embodiments, a thickness of the first paint layer 2 is the same as a depth of the containing grooves 10, further, the thickness of the first paint layer 2 ranges from 0.08 mm to 0.15 mm, and the feeling and the heat insulation effect are the best.

Figure 5:
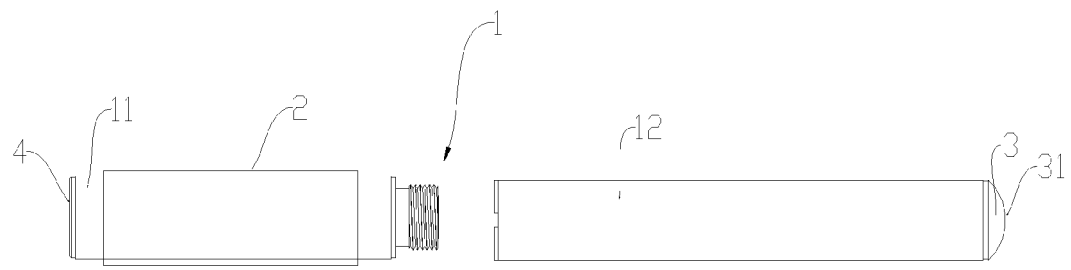
FIG. 5 is a structural schematic view of an electronic cigarette of a fifth embodiment of the present application.

FIG. 5 is a structural schematic view of an electronic cigarette of a fifth embodiment of the present application. In FIG. 5, the first paint layer 2 is arranged at the area, corresponding to the atomizer assembly, of the outer wall of the outer sleeve 1. The outer sleeve 1 comprises an atomizer sleeve 11 and a battery sleeve 12. An atomizer assembly is installed in the atomizer sleeve 11. A battery assembly is installed in the battery sleeve 12, and the battery sleeve 12 is detachably connected to the atomizer sleeve 11. The embodiment adopts threaded connections to detachably connect the battery sleeve 12 to the atomizer sleeve 11. The battery sleeve 12 and the atomizer sleeve 11 can be detachably connected in screw, socket, buckles and other ways. The first paint layer 2 covers on the area, corresponding to the atomizer assembly, of the outer wall of the outer sleeve 1. In this manner, the electronic cigarette has the function of heat insulation and anti-slipping, at the same time, can also save paint.

Further, a suction nozzle is arranged at one end, which is far away from the battery sleeve 12, of the atomizer sleeve 11, a suction nozzle cap 4 is also arranged to maintain the suction nozzle cleaning.

A cigarette end part 3 is mounted at one end, which is far away from atomizer sleeve 11, of battery sleeve 12, a third paint layer 31 is configured on the cigarette end part 3, paint of the third paint layer 31 is luminous paint. The advantages of adopting the luminous paint is that at night the cigarette end part 3 lights to simulate the cigarette burning, can enhance the users' experience. Compared with adopting the LED light-emitting diode, adopting the luminous paint has the advantages of saving the cost of production and enhancing environmental protection.

Figure 6:
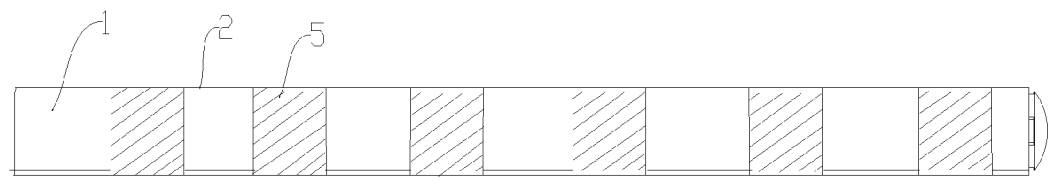
FIG. 6 is a structural schematic view of an electronic cigarette of a sixth embodiment of the present application.

FIG. 6 is a structural schematic view of an electronic cigarette of a sixth embodiment of the present application. In FIG. 6, a second paint layer 5 is added to the electronic cigarette in the base of the embodiment shown in FIG. 1, the second paint layer 5 can be used to set images and/or logos. The second paint layer 5 is several annular paint layers configured separately on the first paint layer 2. Understandably, in other embodiment of the application, the first paint layer 2 and the second paint layer 5 are arranged in parallel on the outer wall of the outer sleeve 1.

Figure 7:
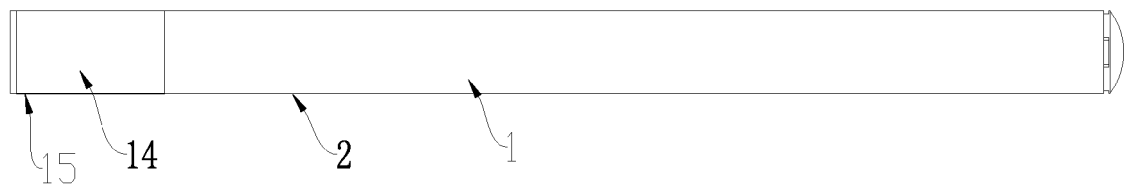
FIG. 7 is a structural schematic view of an electronic cigarette of a seventh embodiment of the present application.

FIG. 7 is a structural schematic view of an electronic cigarette of a seventh embodiment of the present application. In FIG. 7, the first paint r layer 2 fully covers the outer sleeve 1. A suction nozzle part 14 is arranged on the outer sleeve 1, the suction nozzle part 14 is covered with stickers 15. The stickers 15 belongs to food grade, can protect the user's health. Understandably, in other embodiment of the application, the stickers 15 and the first paint layer 2 are coaxial juxtaposed, namely, the outer sleeve 1 is arranged inside of the sticker 15 without setting the first paint layer 2, which can save the cost. Thereby, the outer sleeve 1 can be the atomizer sleeve containing the atomizer assembly, also can be the outer sleeve used for containing the atomizer assembly and the battery assembly.

While the embodiments of the present application are described with reference to the accompanying drawings above, the present application is not limited to the above-mentioned specific implementations. In fact, the above-mentioned specific implementations are intended to be exemplary not to be limiting. In the inspiration of the present application, those ordinary skills in the art can also make many modifications without breaking away from the subject of the present application and the protection scope of the claims. All these modifications belong to the protection of the present application.

What is claimed is:

1. An electronic cigarette, comprising a non-metal outer sleeve and a first paint layer configured along outer wall of the outer sleeve; wherein containing grooves containing the first paint layer is formed on the outer wall of the outer sleeve;

wherein the containing grooves are multiple grooves arranged along the outer wall of the outer sleeve radially separately and surround the outer sleeve; the first paint layer is contained in each of the containing grooves; paint of the first paint layer is UV consolidation paint or rubber paint; a thickness of the first paint layer is the same as a depth of the containing grooves; the thickness of the first paint layer ranges from 0.08 mm to 0.15 mm;

wherein the outer sleeve comprises an atomizer sleeve, a battery sleeve detachably connected to the atomizer sleeve, and a cigarette end part at one end of the battery sleeve, the end is away from the atomizer sleeve, wherein the cigarette end part is provided with a third paint layer, paint of the third paint layer is luminous paint;

wherein the electronic cigarette also comprises a second paint layer for setting images and logos arranged on the first paint layer or on the outer wall of the outer sleeve and in parallel with the first paint layer; and wherein the outer sleeve is provided with a suction nozzle part, the suction nozzle part is covered with stickers; the stickers and the first paint layer are coaxially juxtaposed.

* * * * *